United States Patent
Wotton, III et al.

(10) Patent No.: US 10,864,026 B2
(45) Date of Patent: Dec. 15, 2020

(54) TIBIAL FIXATION PLATE

(71) Applicant: STERIS Instrument Management Services, Inc., Mentor, OH (US)

(72) Inventors: Harold M. Wotton, III, Woodstock, CT (US); Andrew James Kazanovicz, Kuna, ID (US); Matthew Dubois Barnhart, Columbus, OH (US)

(73) Assignee: STERIS Instrument Management Services, Inc., Mentor, OH (US)

( * ) Notice: Subject to any disclaimer, the term of this patent is extended or adjusted under 35 U.S.C. 154(b) by 7 days.

(21) Appl. No.: 16/270,972

(22) Filed: Feb. 8, 2019

(65) Prior Publication Data

US 2020/0253653 A1 Aug. 13, 2020

(51) Int. Cl.
*A61B 17/80* (2006.01)

(52) U.S. Cl.
CPC .................. *A61B 17/8061* (2013.01)

(58) Field of Classification Search
CPC . A61B 17/80; A61B 17/8052; A61B 17/8061; A61B 17/8085
See application file for complete search history.

(56) References Cited

U.S. PATENT DOCUMENTS

| | | | | |
|---|---|---|---|---|
| 5,938,664 A * | 8/1999 | Winquist | ............ | A61B 17/8085 606/283 |
| 6,623,486 B1 * | 9/2003 | Weaver | ............... | A61B 17/8057 606/281 |
| 7,128,744 B2 * | 10/2006 | Weaver | ............... | A61B 17/8057 606/280 |
| 7,341,589 B2 * | 3/2008 | Weaver | ............... | A61B 17/8057 606/282 |
| 8,257,405 B2 * | 9/2012 | Haidukewych | .... | A61B 17/8061 606/280 |

(Continued)

FOREIGN PATENT DOCUMENTS

FR 2 980 967 A1 4/2013
KR 10 2016 0145864 A 12/2016

(Continued)

OTHER PUBLICATIONS

"Save on surgery packs," Shop Veterinary Instrument & Dental Surgical Instruments, website printout from https://spectrumveterinaryinstruments.com, print out date Nov. 15, 2018.

(Continued)

*Primary Examiner* — Eric S Gibson
(74) *Attorney, Agent, or Firm* — Kusner & Jaffe

(57) ABSTRACT

A fixation plate includes a head section, a curved section, and a tail section. The head section includes one or more head apertures formed therethrough. The head apertures are configured to allow screws to respectively pass therethrough at varying angles to attach the head section to a first bone segment. The head section has a bottom surface that is configured to sit flush with the first bone segment. The curved section extends from the head section. The tail section extends from the curved section. The tail section includes one or more tail apertures formed therethrough. The tail apertures are configured to allow screws to respectively pass therethrough at varying angles to attach the tail section to a second bone segment.

7 Claims, 8 Drawing Sheets

(56) References Cited

U.S. PATENT DOCUMENTS

| | | | |
|---|---|---|---|
| 8,262,707 | B2 | 9/2012 | Huebner et al. |
| 8,317,842 | B2* | 11/2012 | Graham ................ A61B 17/86 |
| | | | 606/286 |
| 8,496,665 | B2* | 7/2013 | Cavallazzi ......... A61B 17/1728 |
| | | | 408/202 |
| 8,523,921 | B2 | 9/2013 | Horan et al. |
| 8,911,443 | B2* | 12/2014 | Graham ............ A61B 17/8061 |
| | | | 606/86 B |
| 9,247,946 | B2* | 2/2016 | Cavallazzi ......... A61B 17/1728 |
| 9,283,008 | B2* | 3/2016 | Gonzalez-Hernandez ................. |
| | | | A61B 17/8085 |
| 9,795,424 | B2 | 10/2017 | Austin et al. |
| 10,143,503 | B2 | 12/2018 | Kuroda et al. |
| 10,226,288 | B2* | 3/2019 | Sidebotham ....... A61B 17/8014 |
| 10,258,396 | B2* | 4/2019 | Kazanovicz ....... A61B 17/8061 |
| 10,383,668 | B2* | 8/2019 | Rutledge .......... A61B 17/8061 |
| 10,420,596 | B2* | 9/2019 | Davison ............ A61B 17/8057 |
| 2004/0059335 | A1* | 3/2004 | Weaver ............. A61B 17/8061 |
| | | | 606/280 |
| 2004/0167522 | A1* | 8/2004 | Niederberger ..... A61B 17/8057 |
| | | | 606/286 |
| 2005/0010226 | A1* | 1/2005 | Grady, Jr. ............ A61B 17/809 |
| | | | 606/281 |
| 2005/0070904 | A1* | 3/2005 | Gerlach ............ A61B 17/8014 |
| | | | 606/281 |
| 2006/0173458 | A1* | 8/2006 | Forstein ............ A61B 17/1728 |
| | | | 606/86 B |
| 2006/0212035 | A1 | 9/2006 | Wotton, III |
| 2007/0233106 | A1* | 10/2007 | Horan ................ A61B 17/8061 |
| | | | 606/282 |
| 2008/0140130 | A1* | 6/2008 | Chan ................. A61B 17/8605 |
| | | | 606/280 |
| 2008/0300637 | A1* | 12/2008 | Austin ............... A61B 17/8061 |
| | | | 606/290 |
| 2009/0143825 | A1* | 6/2009 | Graham ................ A61B 17/86 |
| | | | 606/286 |
| 2009/0204121 | A1* | 8/2009 | Cavallazzi ........... A61B 17/808 |
| | | | 606/96 |
| 2010/0030276 | A1* | 2/2010 | Huebner ........... A61B 17/8061 |
| | | | 606/280 |
| 2010/0030277 | A1* | 2/2010 | Haidukewych .... A61B 17/8061 |
| | | | 606/286 |
| 2010/0057133 | A1* | 3/2010 | Simon ................ A61B 17/8061 |
| | | | 606/280 |
| 2010/0152783 | A1 | 6/2010 | Borostyankoi et al. |
| 2011/0218570 | A1* | 9/2011 | Felix ...................... A61L 31/18 |
| | | | 606/246 |
| 2012/0323284 | A1* | 12/2012 | Baker ................ A61B 17/8052 |
| | | | 606/289 |
| 2013/0006246 | A1 | 1/2013 | Dodson |
| 2013/0006312 | A1* | 1/2013 | Graham ............ A61B 17/8061 |
| | | | 606/282 |
| 2013/0289447 | A1* | 10/2013 | Cavallazzi ........... A61B 17/808 |
| | | | 600/587 |
| 2016/0128745 | A1* | 5/2016 | Sidebotham ....... A61B 17/8095 |
| | | | 606/281 |
| 2016/0310184 | A1* | 10/2016 | Kazanovicz ....... A61B 17/1728 |
| 2018/0325568 | A1* | 11/2018 | Wotton ............. A61B 17/8061 |
| 2018/0344371 | A1 | 12/2018 | Monk et al. |
| 2019/0269446 | A1* | 9/2019 | Laird, Jr. ........... A61B 17/8085 |

FOREIGN PATENT DOCUMENTS

| | | |
|---|---|---|
| WO | WO-2016/079504 A1 | 5/2016 |
| WO | WO-2017/164861 A1 | 9/2017 |

OTHER PUBLICATIONS

Brinkman, J.-M. et al., "Osteotomies around the knee," The Journal of Bone and Joint Surgery, Aspects of Current Management, vol. 90-B, No. 12, Dec. 2008, pp. 1548-1557.

International Search Report from corresponding International Patent Application No. PCT/US2020/017133 dated May 29, 2020.

Written Opinion of the International Searching Authority from corresponding International Patent Application No. PCT/US2020/017133 dated May 29, 2020.

* cited by examiner

TIBIAL FIXATION PLATE

FIELD OF THE INVENTION

The present invention relates generally to a bone fixation plate and, more particularly, to a plate configured to fix a tibia in animals, including canines.

BACKGROUND OF THE INVENTION

Bone fixation plates may be used in tibial osteotomy and other procedures to secure two bone segments together. In a tibial plateau leveling osteotomy procedure, for example, a curvilinear cut is made in the canine proximal tibia to separate the metaphysis from the proximal tibia. Next, the metaphysis is rotated to level the tibial plateau. Finally, the metaphysis is fixed to the proximal tibia by a fixation plate.

It is commonly desired by those performing a tibial osteotomy to make the curvilinear cut as proximally high and close to the joint between the tibia and the metaphysis as possible. However, conventional bone fixation plates do not allow such proximally high curvilinear cuts to occur. These proximally high curvilinear cuts are discouraged at least partially due to the large size of a head portion of a conventional bone fixation plate. Further, the large size of head portions and hole locations restricts the ability to manipulate the plate on the bone.

In addition, the geometry of conventional bone fixation plates is straight from a head of the plate to a tail of the plate. This restricts the purchase of the caudal aspect of the proximal tibia and the maximization of central coverage of the mid shaft tibia. Moreover, conventional bone fixation plates do not allow a place for implementation of a skin retractor. As a result, the incisions required when utilizing a conventional bone fixation plate are long.

Finally, conventional bone fixation plates have screw holes that limited or restrictive as to how they allow screws inserted therein to be oriented. In other words, the conventional bone fixation plates do not allow for polyaxial placement of the screws.

The present invention provides an improved bone fixation plate allowing for a high proximal cut in the tibia while promoting caudal purchase of the plate on the proximal tibia and enabling a place for a skin retractor to engage the plate.

SUMMARY OF THE INVENTION

In accordance with an embodiment of the present invention, there is provided a fixation plate. The fixation plate includes a head section, a curved section, and a tail section. The head section includes one or more head apertures formed therethrough. The head apertures are configured to allow screws to respectively pass therethrough at varying angles to attach the head section to a first bone segment. The head section has a bottom surface that is configured to sit flush with the first bone segment. The curved section extends from the head section. The tail section extends from the curved section. The tail section includes one or more tail apertures formed therethrough. The tail apertures are configured to allow screws to respectively pass therethrough at varying angles to attach the tail section to a second bone segment.

In accordance with another embodiment of the present invention, there is provided a fixation plate. The fixation plate includes a head section, a curved section, and a tail section. The head section includes one or more head apertures formed therethrough. The head apertures are configured to allow screws to respectively pass therethrough at varying angles to attach the head section to a first bone segment. The curved section extends from the head section. The tail section extends from the curved section. The tail section includes one or more tail apertures formed therethrough. The tail apertures are configured to allow screws to respectively pass therethrough at varying angles to attach the tail section to a second bone segment. The tail section further includes a recess at a distal end thereof. The recess is configured to enable placement of a lever instrument with the tail section.

An advantage of the present invention is the ability to enable a proximal cut of a tibia closest to a joint that is as high as anatomically possible with a bone fixation plate.

Another advantage of the present invention is the ability to enable a head section of the bone fixation plate to be anatomically contoured for a precise fit.

Still another advantage of the present invention is the ability to allow head and tail sections of the bone fixation plate to make a significant caudal purchase in an osteotomy.

Yet another advantage of the present invention is 15 degrees of angulation allowed by apertures of the fixation plate that are polyaxial.

An additional advantage of the present invention is to allow for a fixed angle construct home position that is enabled by the apertures of the fixation plate.

Another advantage of the present invention is to prevent any screws from entering the joint or entering a bone at a damaging angle through the apertures of a fixation plate when using a home position.

Still another advantage of the present invention is a size reduction of the incision that is enabled by small geometry of the head section of the bone fixation plate.

Yet another advantage of the present invention is the ability of a surgeon using the bone fixation plate to use a geometric feature in the head section of the fixation plate to place bone reduction forceps on the fixation plate and on a portion of the tibia below the cut, which allows for the application of compression.

An additional advantage of the present invention is the enabling of more caudal purchase through geometry of the bone fixation plate at a transition between the head section and the tail section.

Another advantage of the present invention is the geometric design of the distal end of the bone fixation plate, which allows the surgeon to place a retractor on the distal end of the bone fixation plate, use the retractor without slipping off the plate, and retract soft tissue allowing for a smaller incision.

These and other advantages will become apparent from the following description of illustrated embodiments taken together with the accompanying drawings and the appended claims.

BRIEF DESCRIPTION OF THE DRAWINGS

The invention may take physical form in certain parts and arrangement of parts, a preferred embodiment of which will be described in detail in the specification and illustrated in the accompanying drawings which form a part hereof, and wherein.

DETAILED DESCRIPTION OF THE INVENTION

It is initially noted that, in the embodiments described herein, the standard anatomical terminology used corresponds to the standard anatomical position of a canine or an animal having hind limb anatomy corresponding with that of a canine. Application of the invention embodiments described herein is not restricted to a canine or an animal having hind limb anatomy corresponding with that of a canine. However, while it is contemplated that the invention could be applied to a human or an animal having lower leg anatomy corresponding with that of a human, the standard anatomical position of a human is different from the standard anatomical position of a canine. Thus, the standard anatomical terminology describing the application of the invention with respect to a canine or an animal having hind limb anatomy corresponding with that of a canine will not correspond to the standard anatomical terminology necessary to describe application of the invention with respect to a human or an animal having lower leg anatomy corresponding with that of a human.

Figure 1:
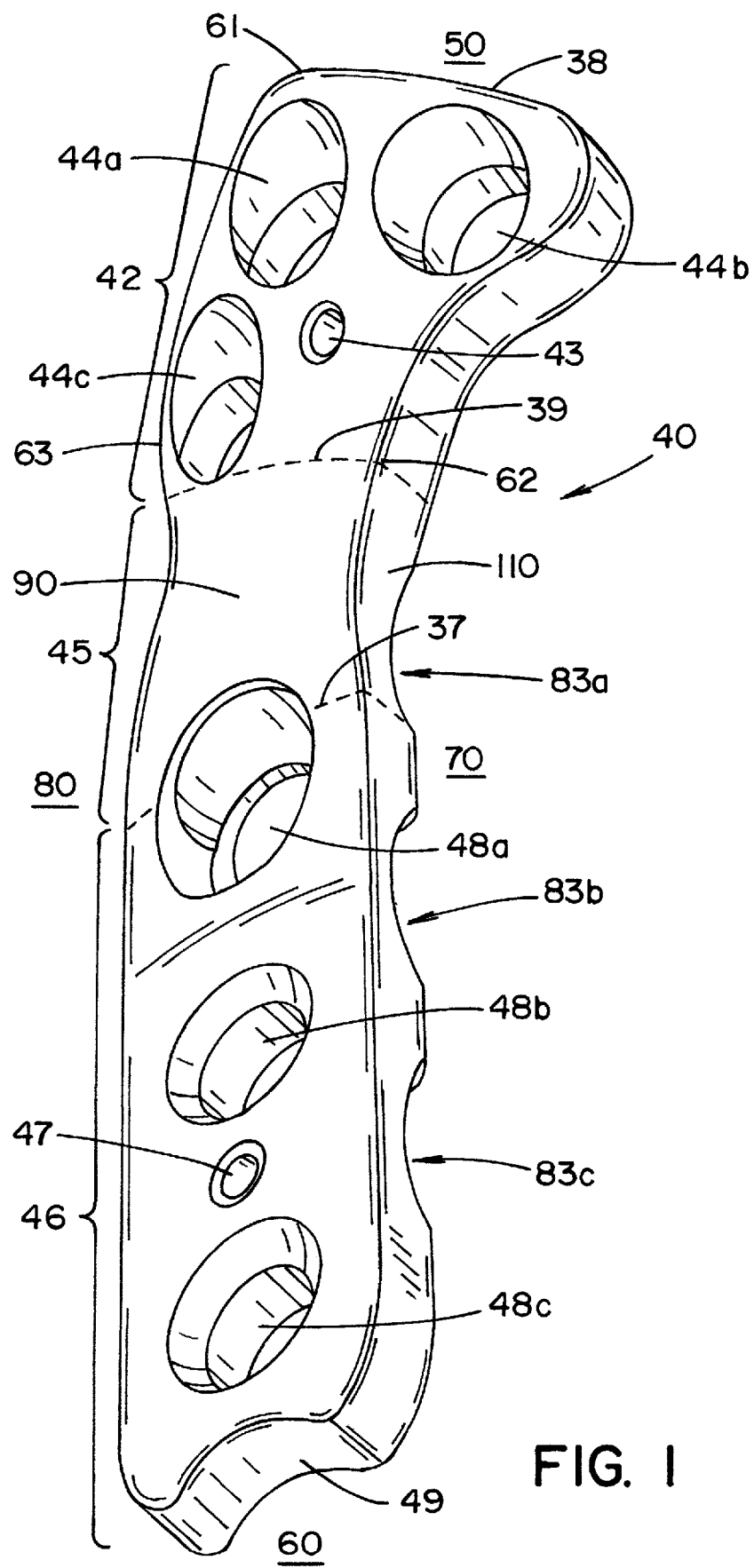
FIG. 1 is an example illustration of a plan view of a tibial fixation plate according to an embodiment of the present invention.
Figure 2:
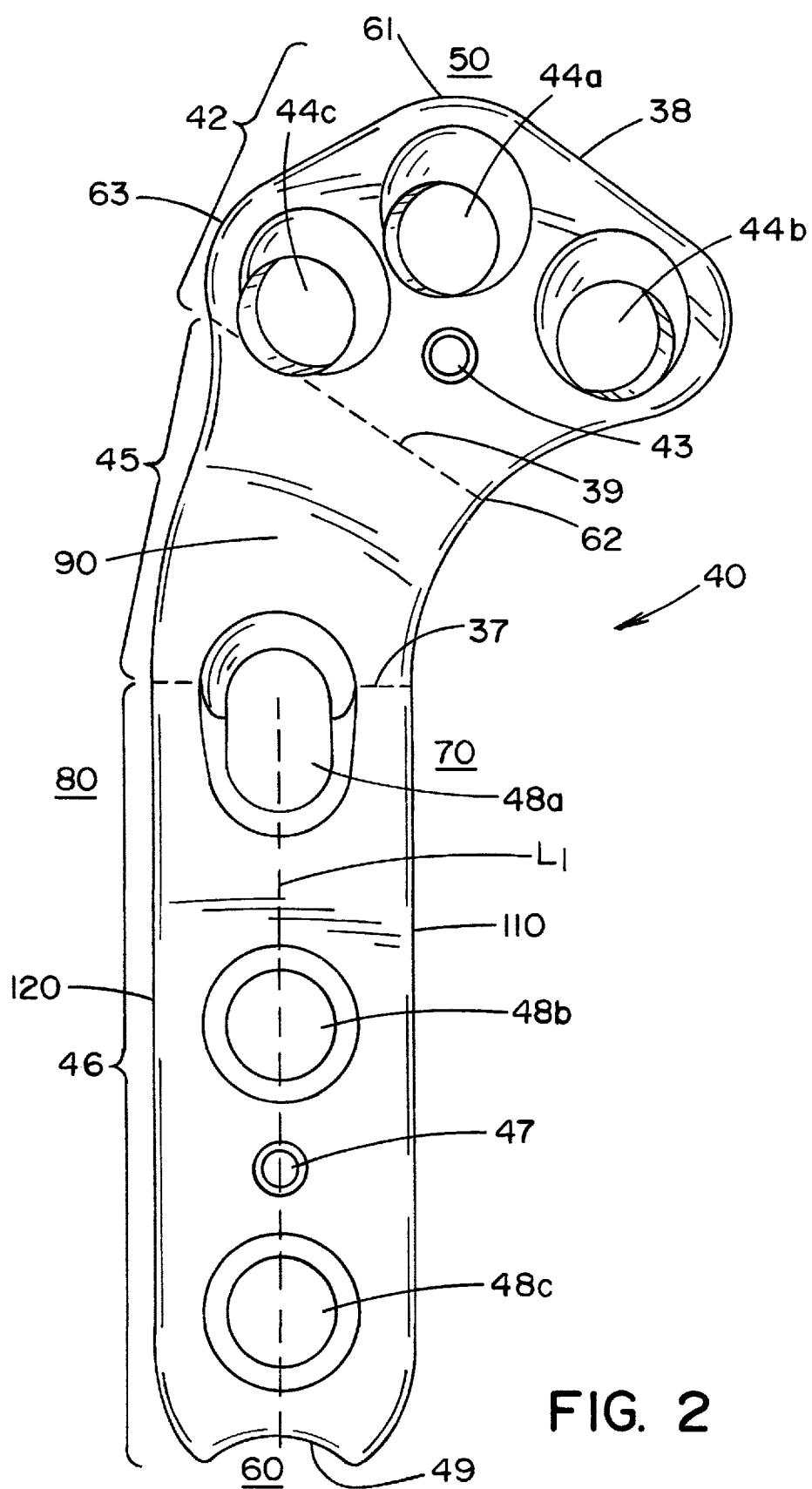
FIG. 2 is an example illustration of a top surface view of a tibial fixation plate according to an embodiment of the present invention.
Figure 3:
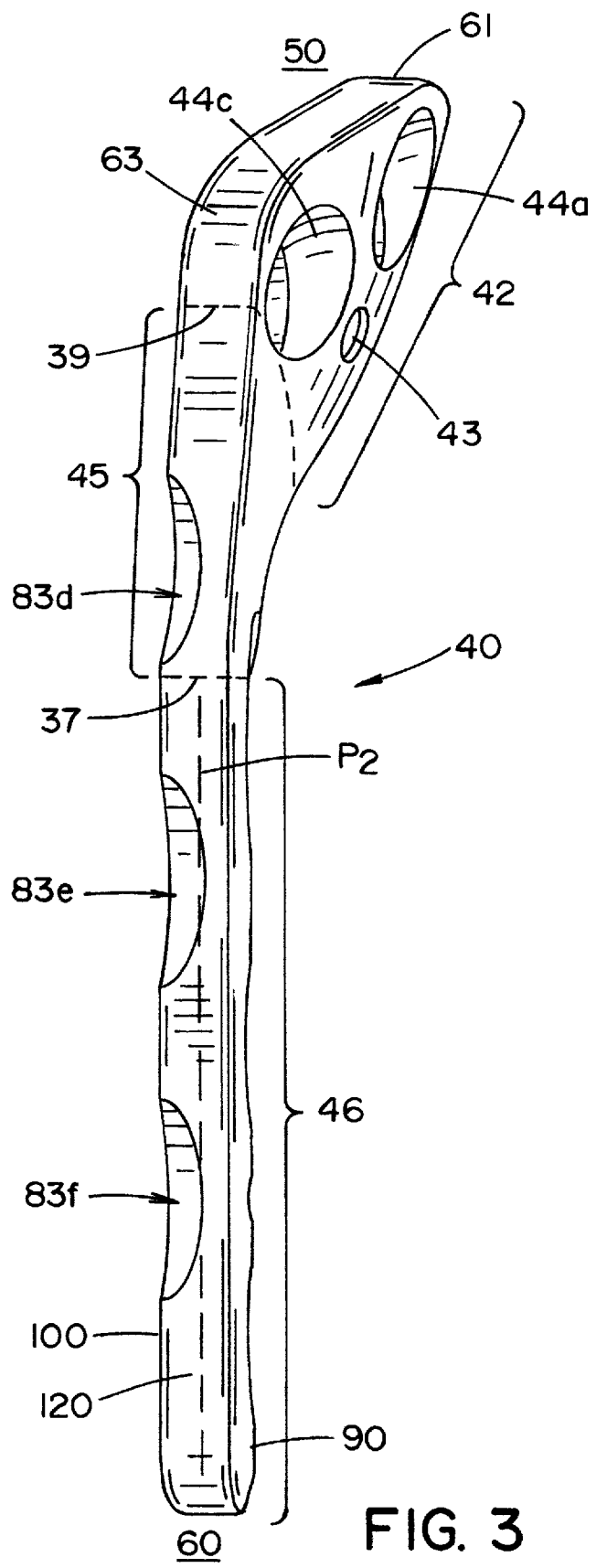
FIG. 3 is an example illustration of a cranial surface view of a tibial fixation plate according to an embodiment of the present invention.
Figure 4:
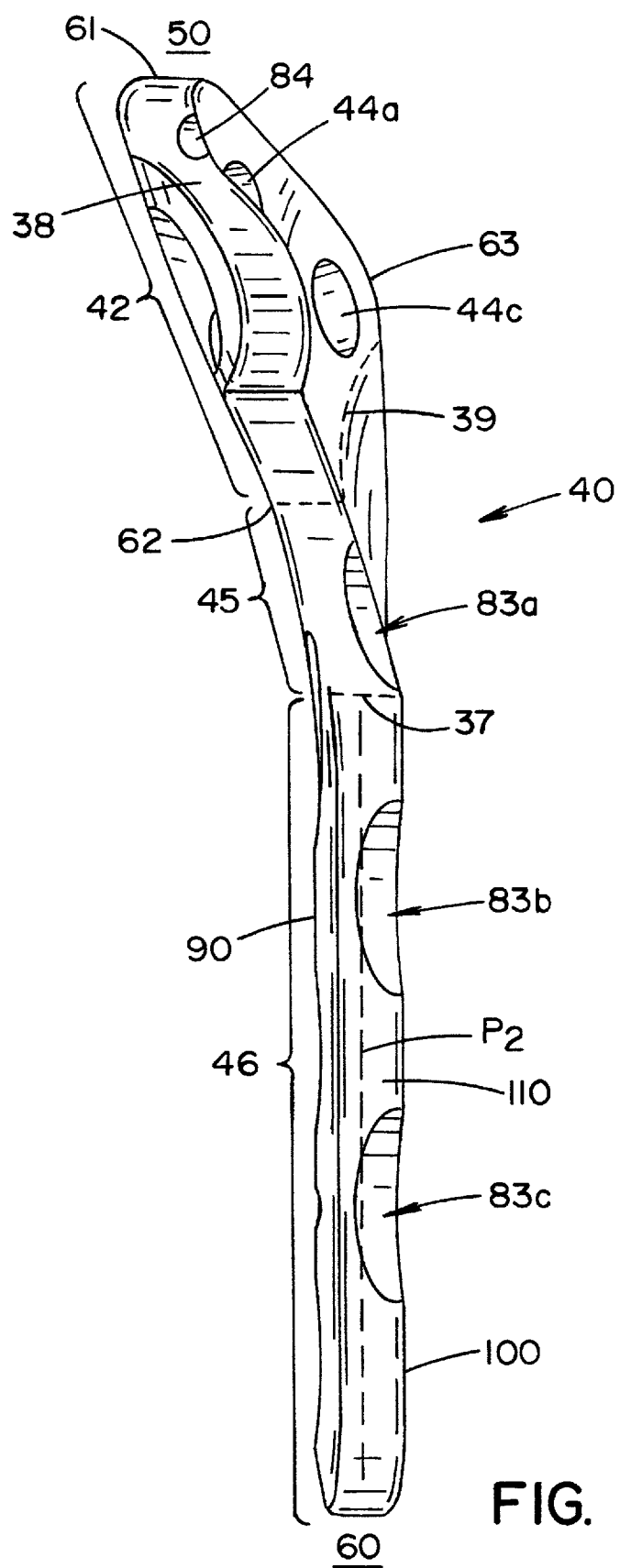
FIG. 4 is an example illustration of a caudal surface view of a tibial fixation plate according to an embodiment of the present invention.
Figure 5:
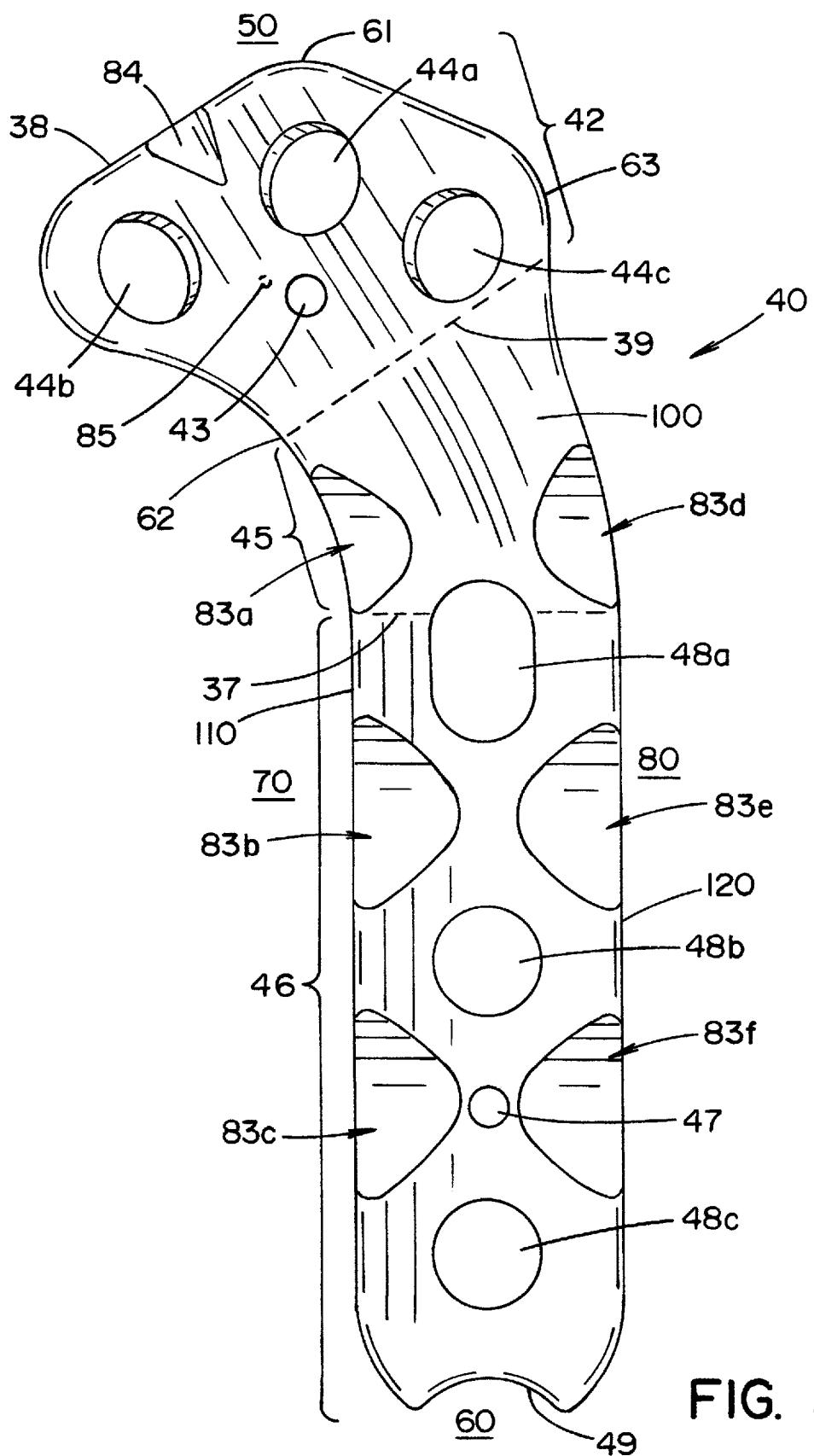
FIG. 5 is an example illustration of a bottom surface view of a tibial fixation plate according to an embodiment of the present invention.
Figure 6:
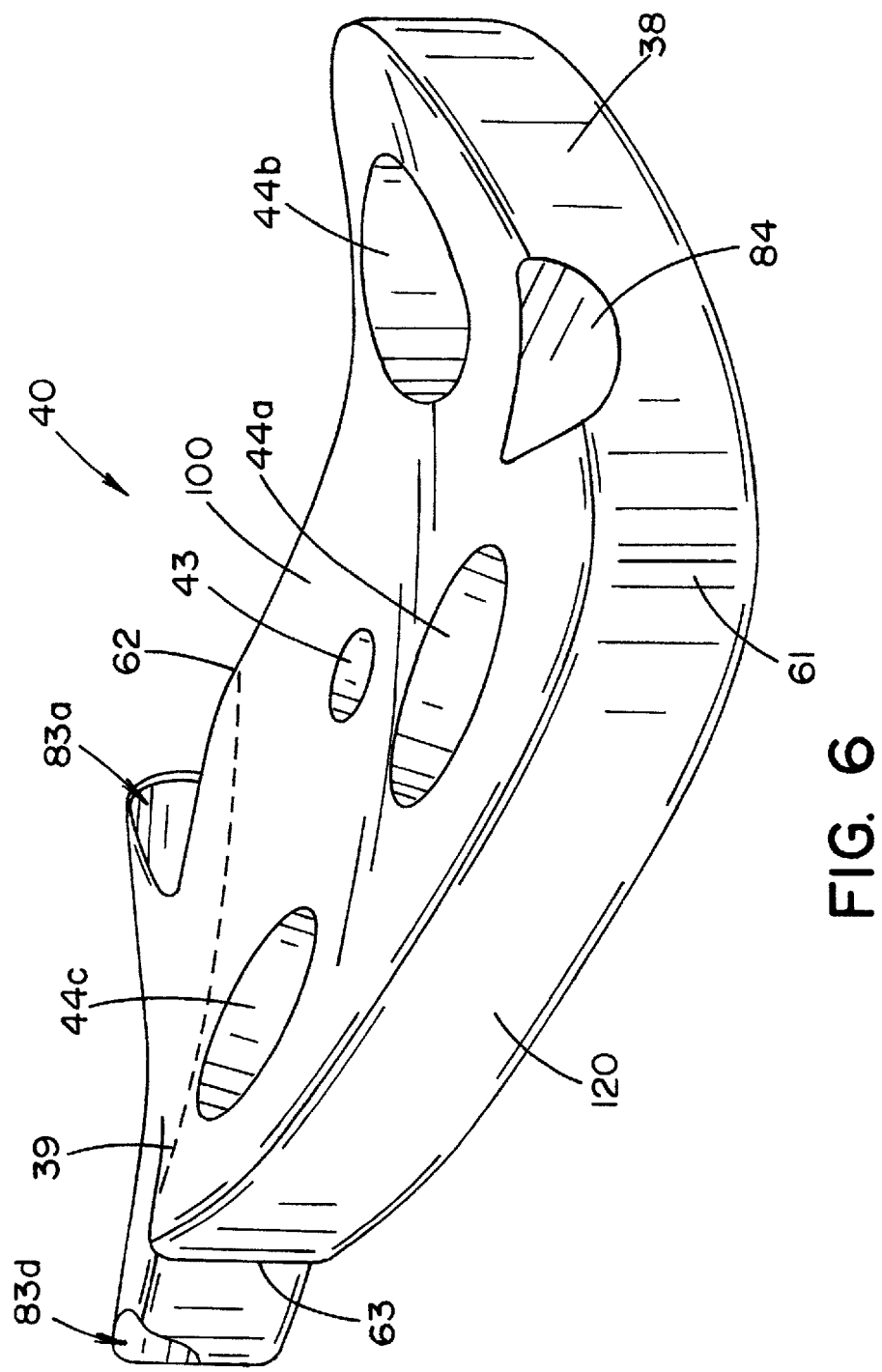
FIG. 6 is an example illustration of a proximal end plan view of a tibial fixation plate from a bottom surface perspective according to an embodiment of the present invention.
Figure 7:
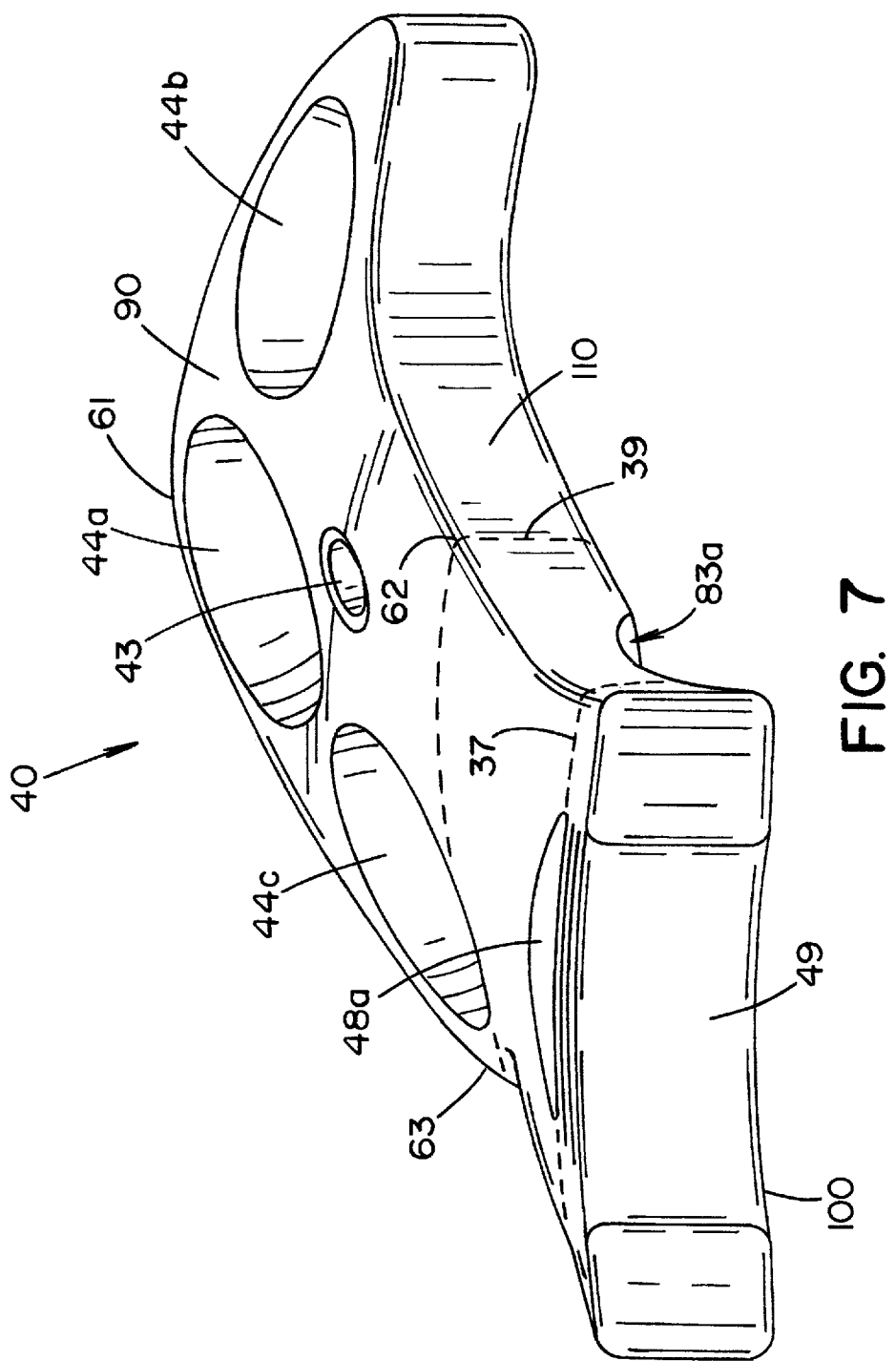
FIG. 7 is an example illustration of a distal end plan view of a tibial fixation plate from a top surface perspective according to an embodiment of the present invention.
Figure 8:
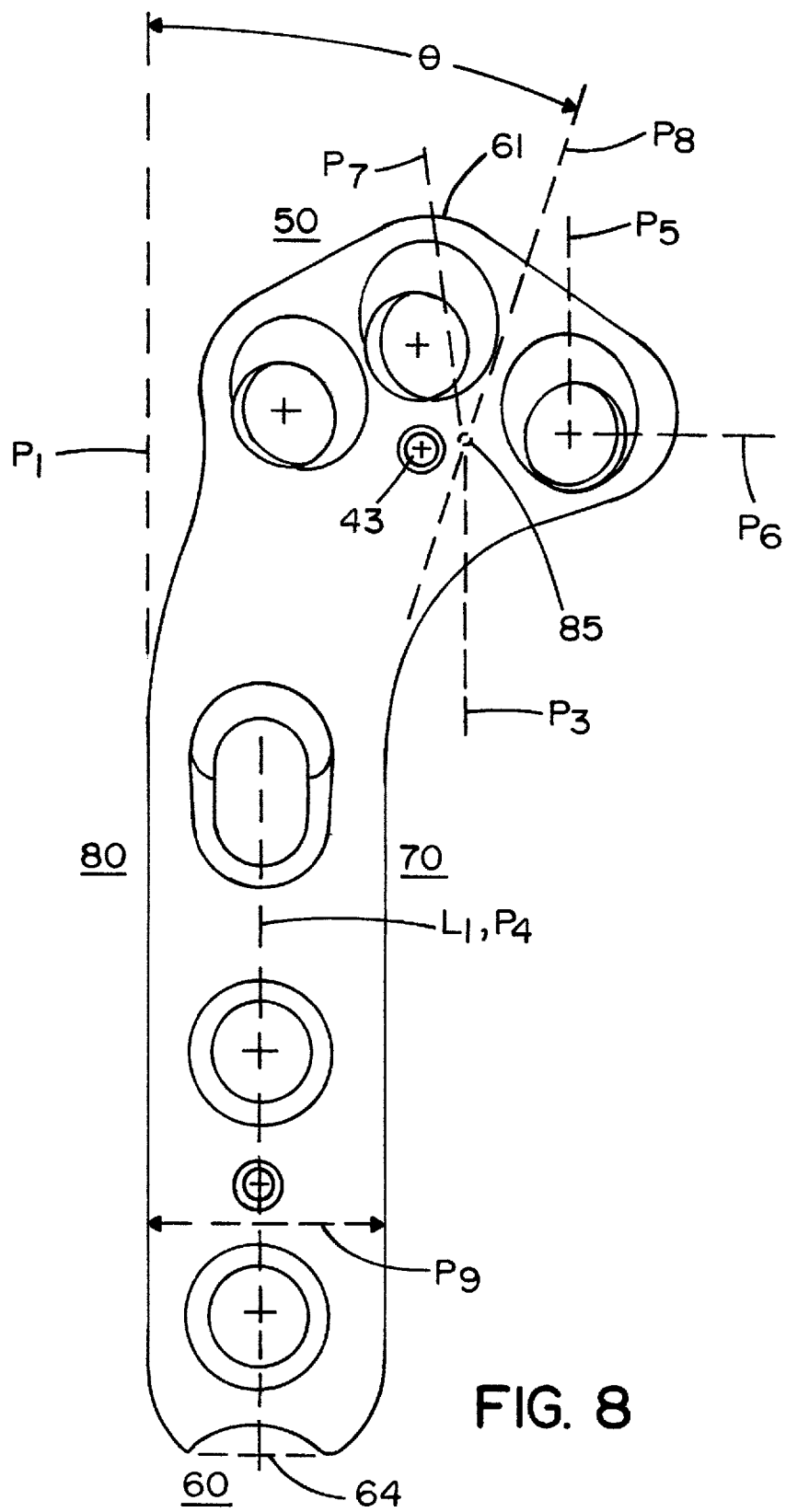
FIG. 8 is another example illustration of a top surface view of a tibial fixation plate according to an embodiment of the present invention, in which dimensional aspects of the tibial fixation plate are illustrated.

Referring now to the drawings wherein the showings are for the purposes of illustrating an embodiment of the invention only and not for the purposes of limiting same, FIGS. 1-8 are illustrations of tibial fixation plate 40 from various aspects.

Tibial fixation plate 40 is defined between proximal end 50, distal end 60, caudal side 70 and cranial side 80 thereof. Tibial fixation plate 40 has distal surface 49, top surface 90, bottom surface 100, caudal surface 110, and cranial surface 120. Bottom surface 100 generally faces the tibia and is in contact with or fixed in place on the tibia when in use. Bottom surface 100 is a surface opposing top surface 90.

Tibial fixation plate 40 includes three distinct sections—head section 42, curved section 45, and tail section 46. Head section 42 is generally diamond shaped and positioned at proximal end 50. Head section extends from proximal corner 61 of head section 42 at proximal end 50 toward distal end 60 to distal corner 62 of head section 42. Head section 42 has a width that initially increases with distance distally away from proximal corner 61 of head section 42 distally toward distal corner 62 of head section 42. Curved section 45 is positioned between head section 42 and tail section 46. Proximal interface 39 marks the proximal end of curved section 45 and the distal end of head section 42. Distal interface 37 marks the distal end of curved section 45 and the proximal end of tail section 46. Tail section 46 extends from distal interface 37 with curved section 45 to distal end 60 of tibial fixation plate 40. Tail section 46 is connected to head section 42 by curved section 45. Both caudal surface 110 and cranial surface 120 extend between top surface 90 and bottom surface 100.

Head section 42 is anatomically contoured to precisely fit the tibia. Head section 42 is also shaped to allow tibial fixation plate 40 to be placed in multiple locations on the tibia to achieve the desired fixation. Head section 42 is further shaped to allow for significant causal purchase in osteotomy.

Head section 42 includes head provisional opening 43 and head apertures 44a, 44b, and 44c. Head apertures 44a, 44b, and 44c enable head section 42 to be fixed to one tibial segment (e.g., the medial segment). Head provisional opening 43 enables temporary placement of fixation plate 40 on the tibia to provisionally fix tibia elements or visualize a desired trajectory for screws to be inserted through head apertures 44a, 44b, and 44c.

Head apertures 44a, 44b, and 44c are designed to ensure that screw ends do not collide with any other screw end inside the tibia outside the far side of the tibia. If screws were to collide in the tibia, they would not be able to be fully seated. Head apertures 44a, 44b, and 44c increase the holding power of tibial fixation plate 40 so that if tibial fixation plate 40 was pulled off the tibia, the material between the screws would need to break out, which would require more force than is possible to apply.

Head apertures 44a, 44b, and 44c are configured to receive fixing or locking means, such as screws. The center point of head aperture 44a is closest to proximal corner 61 of head section 42 at proximal end 50. If locking screws are used, because the screw heads thereof lock into tibial fixation plate 40, they cannot change their angle in tibial fixation plate 40 once fully seated. Standard non-locking screws can change their angle if a load is applied to tibial fixation plate 40 (because they do not lock). Therefore, when using locking screws that have their heads fixed inside tibial fixation plate 40, the loads required to get tibial fixation plate 40 to be pulled off the tibia are significantly higher.

A distance from a center point of head provisional opening 43 to first plane $P_1$ established by cranial side 80 of tibial fixation plate 40 at tail section 46 along a plane that is perpendicular to first plane $P_1$ is in a range from 12.5 mm to 14.5 mm. A distance from a center point of head aperture 44c to first plane $P_1$ along a plane that is perpendicular to first plane $P_1$ is between 6 mm and 7 mm. A distance from a center point of head aperture 44a to first plane $P_1$ along a plane that is perpendicular to first plane $P_1$ is between 11 mm and 13.5 mm. A distance from a center point of head aperture 44b to first plane $P_1$ along a plane that is perpendicular to first plane $P_1$ is between 18 mm and 21.5 mm. A distance from a center point of head provisional opening 43 to distal end 60 of tibial fixation plate 40 is between 46 mm and 55 mm. A distance from a center point of head aperture 44c and distal end 60 is between 48 mm and 56 mm. A distance from a center point of head aperture 44b and distal end 60 is between 47 mm and 54 mm. A distance from a center point of head aperture 44a and distal end 60 is between 52 mm and 60 mm. The center points of head apertures 44b and 44c are slightly offset in a range between 1 and 2 mm. A distance between proximal corner 61 of head section 42 and distal end 60 is between 55 mm and 66 mm.

The width of head section 42 reaches a maximum distance at the approximate middle of head section 42 (i.e. the middle of the diamond) before the width begins to gradually decrease again in the direction of distal corner 62 of head section 42, at which head section 42 smoothly joins curved section 45 at proximal interface 39. Proximal interface 39 extends across tibial fixation plate 40 from distal corner 62 of head section 42 toward cranial side 80 to a point adjacent cranial corner 63 of head section 42. Proximal interface 39 is generally parallel with and opposite to proximal caudal edge 38 of head section 42.

With respect to curved section 45 and tail section 46, head section 42 projects toward caudally. Curved section 45 contributes to the caudal projection of head section 42, as curved section 45 curves caudally away from tail section 46 between distal interface 37 and proximal interface 39. The angle of the curve formed by curved section 45 beginning from a middle portion of distal interface 37 and extending about a circular plane that has a diameter of in a range of 25 mm to 29 mm is in a range of 71 to 84 degrees. This ensures that tail section 46, discussed below, is central on a long axis of the tibia. It also ensures that cranial corner 63 of head section 42 is very cranial to allow for a screw in the largest part of the tibia. This allows for optimized plate positioning.

Tail section 46 includes tail provisional opening 47 and tail apertures 48a, 48b, and 48c. Tail provisional opening 47 serves similar purposes as does head provisional opening 43. Tail apertures 48a, 48b, 48c enable tail section 46 to be fixed to another bone segment (e.g., the distal segment (diaphysis)). First longitudinal axis $L_1$ extends from the center of the distal end 60, along the length of tail section 46, and through distal interface 37. While the center points of head apertures 44a, 44b, and 44c are not aligned with each other, the center points of tail apertures 48a, 48b, and 48c are aligned with each other on first longitudinal axis $L_1$. In addition, the center points of head apertures 44a, 44b, and 44c are not aligned with the center points of tail apertures 48a, 48b, and 48c. This offset puts tail section 46 more cranial than head section 42.

A thickness of tail section 46 is in a range between 2 and 4 mm. A radius of tail section 46 about top surface 90 is in a range of 58 mm to 69 mm. A radius of tail section 46 about bottom surface 100 is in a range of 54 mm to 66 mm. A width of tail section 46 between caudal side 70 and cranial side 80 along plane $P_9$ that is perpendicular to plane $P_1$ is in a range of 10 mm to 12 mm.

Distances from center points of tail apertures 48a, 48b, and 48c and tail provisional opening 47 to first plane $P_1$ along respective planes that are perpendicular to first plane $P_1$ are between 5 mm and 6 mm. A distance between tail aperture 48b and the center point of tail aperture 48c is in a range 11 mm to 13 mm. A distance between the center point of tail aperture 48b or the center point of tail aperture 48c and tail provisional opening 47 is in a range of 5 mm to 7 mm. A distance from a center point of tail aperture 48c and distal end 60 of tibial fixation plate 40 is between 6 mm and 7 mm.

Tail aperture 48a is positioned closer to head section 42 than tail apertures 48b and 48c. In this example, tail aperture 48a extends from tail section 46 to curved section 45 through distal interface 37. Also, in this example, tail aperture 48a is generally obround in shape, thereby enabling the use of screws having unique heads or more than one screw therein. Tail aperture 48a is generally positioned so that a distance between a center point of tail aperture 48a and distalmost point 64 of tibial fixation plate 40 along first longitudinal axis $L_1$ is in a range of 27 mm to 33 mm. In addition, tail aperture 48a has a length along first longitudinal axis $L_1$ in a range of 5.5 mm to 7.5 mm and a width along a plane perpendicular to first longitudinal axis $L_1$ at a center point thereof in a range of 4 mm to 5 mm.

Tail aperture 48a serves as a "combination" aperture that may be used for either compression or locking/fixing. In addition, the shape of tail aperture 48a allows screws to be placed more cranially, which is more central to the long axis of the tibia and a much better place to put a screw.

Tail apertures 48b and 48c are generally circular in shape and positioned so that the center points of tail apertures 48a, 48b, and 48c lie on first longitudinal axis $L_1$. Tail apertures 48b and 48c can accept a locking screw or a standard non-locking screw.

In the example shown herein, apertures 44a, 44b, 44c, 48a, 48b, and 48c are not threaded. By providing a tibial fixation plate 40 having apertures 44a, 44b, 44c, 48a, 48b, and 48c containing no pre-formed screw threads, a surgeon can place a screw at whatever angle is necessary and/or appropriate for that application.

For example, when tibial fixation plate 40 is made from a metal, specifically designed locking screws may be enabled by fixation plate 40 to be placed with a plurality of degrees of freedom. In one case, apertures 44a, 44b, 44c, 48a, 48b, and 48c can be set at specific angles to allow a surgeon to take advantage thereof. The angles can be altered by a plurality of degrees in any direction by screws that possess a plurality of interrupted threads.

For example, screws possessing four sets of interrupted threads could enter apertures 44a, 44b, 44c, 48a, 48b, and 48c of the fixation plate 40 at an angulation of up to 15 degrees in any direction. By having the interrupts in the threads, the screw threads have 4 starting positions (4 interrupts). With these multiple starting positions, the screw threads can enter the plate at four different angles or locations, thereby allowing the screw to be placed at multiple angles.

The non-threaded apertures 44a, 44b, 44c, 48a, 48b, and 48c support standard locking or non-locking screws as well as self-locking screws, which are provided with a screw thread that may 'self-tap' into apertures 44a, 44b, 44c, 48a, 48b, and 48c. In the case in which tibial fixation plate 40 is a polymer plate, the self-tapping screw thread results in the forming of screw threads in apertures 44a, 44b, 44c, 48a, 48b, and 48c as the screws are inserted.

When tibial fixation plate 40 has at least an inner surface of apertures 44a, 44b, 44c, 48a, 48b, and 48c made from polymers, such as a bioabsorbable blend of Poly Lacitdes or Poly L/D/L Lactide (PLDLA), this 'self-tapping' feature is enabled, as the material in apertures 44a, 44b, 44c, 48a, 48b, and 48c is soft enough for the screw threads to be formed therein upon insertion of a screw. In some embodiments, only the inner surfaces of apertures 44a, 44b, 44c, 48a, 48b, and 48c need to be made from this deformable material. In other embodiments, the entire tibial fixation plate 40 may be made from this material.

In some embodiments, tibial fixation plate 40 may be machined out of surgical implant grade 316L stainless steel or titanium. In some embodiments, tibial fixation plate 40 may include the addition of further additives. For example, tibial fixation plate 40 may be a blend of PLDLA and biphasic calcium phosphate with a proprietary binding agent, with the inclusion of further additives, e.g. 60% PLDLA/40% biphasic calcium phosphate. The 40% biphasic calcium phosphate is 70% hydroxyapatite and 30% tricalcium phosphate (TCP). For example, in some embodiments, the blend of PLDLA may include TCP, which supports and stimulates bone growth. In other examples, bioglass may be added to increase the strength of tibial fixation plate 40. In other embodiments, pharmaceuticals or other healing compounds may be added and used within the material. As tibial fixation plate 40 is absorbed by the body the pharmaceutical will then slowly be released at tibial fixation plate 40. By using a bioabsorbable polymer, tibial fixation plate 40 may be at least partially absorbed into the body after the bone has healed. Such bioabsorbable polymers are also more biocompatible than metal. By using such materials, the chance of infection is also reduced, because the surface of a bioabsorbable implant is constantly changing. As such, it is difficult for bacteria to grow.

In some embodiments, tibial fixation plate 40 may be made from a radiolucent material to enable only the bone growth to be seen when x-rayed, but not tibial fixation plate 40 itself. This would give the surgeon a clear and unobstructed view of the bone growth during healing.

The screws that may be used with tibial fixation plate 40 may be made from a polymer such as a bioabsorbable polymer, or may be made from a biocompatible metal, including examples such as titanium or stainless steel. Other biocompatible materials as are known in the art may also be used.

Reduced areas of thickness may be achieved by providing caudal recessed channels 83a, 83b and 83c in corresponding areas of caudal surface 110 and bottom surface 100 and cranial recessed channels 83d, 83e, and 83f in corresponding areas of cranial surface 120 and bottom surface 100. Recessed channels 83a, 83b, 83c, 83d, 83e, and 83f help to reduce the amount of contact that bottom surface 100 of tibial fixation plate 40 has with the tibia when tibial fixation plate 40 is fixed in place. Further, any bending forces applied to tibial fixation plate 40 would be concentrated at recessed channels 83a, 83b, 83c, 83d, 83e, and 83f instead of being concentrated in areas of tibial fixation plate 40 that would normally be subject to bending force.

For example, tail apertures 48a, 48b, and 48c in which locking screws are positioned are areas of tibial fixation plate 40 that would commonly be subject to bonding force. In the examples illustrated herein, recessed channels 83a, 83b, 83c, 83d, 83e, and 83f under the plate are placed between corresponding tail apertures 48a, 48b, and 48c. This promotes bending of tibial fixation plate 40 at recessed channels 83a, 83b, 83c, 83d, 83e, and 83f during further contouring of tibial fixation plate 40 instead of through the tail apertures 48a, 48b, and 48c.

In the examples illustrated herein, recessed channels 83a and 83d correspond with tail aperture 48a, recessed channels 83b and 83e correspond with tail aperture 48b, and recessed channels 83c and 83f correspond with tail aperture 48c. As a result of the placement of recessed channels 83a, 83b, 83c, 83d, 83e, and 83f, loosening or possible fracture of the screws and/or with corresponding tail apertures 48a, 48b, and 48c may be reduced.

Tibial fixation plate 40 described herein is shaped to have a non-uniform cross-sectional profile, as shown in FIGS. 3, 4, 6, and 7. For example, tail section 46 containing tail apertures 48b and 48c may have a generally uniform linear cross section or profile that extends in a second plane $P_2$. However, tail aperture 48a is illustrated as being split by distal interface 37 and thereby positioned in both curved section 45 and tail section 46. Beginning at distal interface 37 and continuing through curved section 45, on caudal side 70 of tibial fixation plate 40, top surface 90, bottom surface 100, and caudal surface 110 are illustrated as extending in an upward direction away from the tibia and second plane $P_2$ at an angle.

As such, tail aperture 48a and recessed channels 83a and 83d angle in the upward direction away from second plane $P_2$ as well. Further, on caudal side 70, top surface 90, bottom surface 100, and caudal surface 110 continue to be angled in an upward direction away from second plane $P_2$ across proximal interface 39 and into head section 42. In embodiments described herein, on caudal side 70, curved section 45 and head section 42 may be angled upward away from second plane $P_2$ in a range from 12 degrees to 20 degrees.

On cranial side 80, top surface 90, bottom surface 100, and cranial surface 120 begin to be angled in an upward direction away from second plane $P_2$ at proximal interface 39 and head section 42. In embodiments described herein, on cranial side 80, head section 42 may be angled away from second plane $P_2$ in a range from 12 degrees to 20 degrees.

Top surface 90 and bottom surface 100 at head section 42 may also be curved, so that top surface 90 at head section 42 is convex whereas bottom surface 100 at head section 42 is concave. For example, a downward bend of head section 42 from origin 85 of tibial fixation plate 40 toward cranial side 80 to cranial corner 63 at bottom surface 100 allows cranial side 80 of tibial fixation plate 40 to sit flush with a proximal part of the tibia to reduce the need for a surgeon to contour tibial fixation plate 40 intraoperatively. Origin 85 of tibial fixation plate 40 is defined as a center of a distal aspect of tibial fixation plate 40.

The downward bend of head section 42 from origin 85 of tibial fixation plate 40 toward cranial side 80 to cranial corner 63 at bottom surface 100 is oriented in a range of 32 degrees to 38 degrees. An arc of the downward bend of head section 42 from origin 85 of tibial fixation plate 40 toward cranial side 80 to cranial corner 63 at bottom surface 100 has a radius between 14 mm and 15 mm.

Origin 85 of tibial fixation plate 40 is between 52 mm and 53 mm from distal end 60 along third plane $P_3$ parallel to first plane $P_1$, where third plane $P_3$ is between 10 mm and 11 mm from fourth plane $P_4$. Fourth plane $P_4$ corresponds with first longitudinal axis $L_1$ at distalmost point 64 of tibial fixation plate 40. Origin 85 of tibial fixation plate 40 is also between 4 mm and 5 mm in distance from fifth plane $P_5$, which is parallel to first plane $P_1$ and intersects the center point of head aperture 44b. Finally, origin 85 of tibial fixation plate 40 is about 1 mm in distance from sixth plane $P_6$, which runs through the center point of head aperture 44b perpendicular to fifth plane $P_5$. Origin 85 of tibial fixation plate 40 is also positioned along eighth plane $P_8$, which extends tangent to curved section 45 at caudal side 70 and intersects first plane $P_1$ at an angle θ in a range of 24 degrees to 28 degrees.

In addition, a downward twist of head section 42 from origin 85 of tibial fixation plate 40 along seventh plane $P_7$ toward caudal side 70 allows caudal side 70 of tibial fixation plate 40 to sit flush with the proximal part of the tibia to reduce the need for a surgeon to contour tibial fixation plate 40 intraoperatively. A downward twist of head section 42 from origin 85 of tibial fixation plate 40 along seventh plane $P_7$ toward caudal side 70 is between 29 degrees to 35 degrees. Seventh plane $P_7$ extends through origin 85 of tibial fixation plate 40 proximally to a point at or adjacent to proximal corner 61.

Head section 42 may bend through origin 85 of tibial fixation plate 40 upward to accommodate the tibial anatomy to reduce the need to perform additional bending during surgery. Head section 42 may bend upward along seventh plane $P_7$ in a range of 22 degrees to 25 degrees where a radius of an arc of the upward bend is between 23 mm and 26 mm.

Distal surface 49 is defined between top surface 90, bottom surface 100, caudal surface 110, and cranial surface 120 at distal end 60 of tibial fixation plate 40. Distal surface 49 has a recess formed therein that resembles a "toe cut". The recess allows for a small incision site where a surgeon can use a lever instrument, such as a retractor, to stretch the skin to allow screws to be inserted into tail apertures 48*a*, 48*b*, and 48*c* to secure tail section 46. The design of distal surface 49 enables the use of level instrument or retractor without being fearful of slippage of level instrument or retractor off tibial fixation plate 40.

In some embodiments, bottom surface 100 at head section 42 may include mark 84 extending distally into head section 42 from caudal edge 38 of head section 42. Mark 84 may provide an indication of a location of tibial fixation plate 40 over the tibia. In some embodiments, where tibial fixation plate 40 is made from metal, mark 84 may be machined onto bottom surface 100 at head section 42. Mark 84 may be utilized to designate a home position for placement of head and tail sections 42 and 46 of tibial fixation plate 40 at preferred locations to inhibit screws passing through apertures 44*a*, 44*b*, 44*c*, 48*a*, 48*b*, and 48*c* from entering joints or being secured at damaging or undesirable angles.

The foregoing descriptions are example embodiments of the present invention. It should be appreciated that these embodiments are described for purposes of illustration only, and that numerous alterations and modifications may be practiced by those skilled in the art without departing from the spirit and scope of the invention. It is intended that all such modifications and alterations be included insofar as they come within the scope of the invention as claimed or the equivalents thereof.

Having described the invention, the following is claimed:

1. A fixation plate, comprising:
    a head section comprising one or more head apertures formed therethrough, the head apertures being configured to allow screws to respectively pass therethrough at varying angles to attach said head section to a first bone segment, the head section having a bottom surface that is configured to sit flush with the first bone segment;
    a curved section extending from the head section; and
    a tail section extending from said curved section, the tail section comprising one or more tail apertures formed therethrough, the tail apertures being configured to allow screws to respectively pass therethrough at varying angles to attach said tail section to a second bone segment,
    wherein the bottom surface of the head section comprises a mark extending distally into the head section from a caudal edge of the head section, the mark being configured to enable positioning of the head and tail sections at locations to inhibit the screws from passing through the head and tail apertures at undesirable angles.

2. The fixation plate according to claim 1, wherein the head and tail apertures are configured to allow the screws to pass therethrough at angles up to and including 15 degrees.

3. The fixation plate according to claim 1, wherein a caudal one of the head apertures located nearest a caudal side of the fixation plate is offset from a cranial one of the head apertures located nearest a cranial side of the fixation plate.

4. The fixation plate according to claim 1, wherein the head section projects caudally from the tail section, and
    wherein the curved section curves caudally away from the tail section to project the head section caudally from the tail section.

5. The fixation plate according to claim 1, wherein a radius of a top surface of the tail section is greater than a radius of a bottom surface of the tail section.

6. The fixation plate according to claim 1, wherein the tail section further comprises a recess at a distal end thereof, the recess being configured to enable placement of a lever instrument with the tail section.

7. The fixation plate according to claim 1, wherein the head section includes a cranial corner on a cranial side of the head section, the cranial corner protruding cranially away from a caudal side of the head section.

* * * * *